(12) United States Patent
Willers

(10) Patent No.: US 10,438,417 B2
(45) Date of Patent: *Oct. 8, 2019

(54) DEVICE AND METHOD FOR EDITING A VIRTUAL, THREE-DIMENSIONAL DENTAL MODEL BY MEANS OF A VIRTUAL TOOL

(71) Applicant: DENTSPLY SIRONA Inc., York, PA (US)

(72) Inventor: Ulf Willers, Seeheim-Jugenheim (DE)

(73) Assignee: DENTSPLY SIRONA Inc., York, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/614,279

(22) Filed: Jun. 5, 2017

(65) Prior Publication Data
US 2017/0265973 A1 Sep. 21, 2017

Related U.S. Application Data

(63) Continuation of application No. 13/992,368, filed as application No. PCT/EP2011/072851 on Dec. 15, 2011, now Pat. No. 9,668,836.

(30) Foreign Application Priority Data

Dec. 15, 2010 (DE) ........................ 10 2010 063 124

(51) Int. Cl.
*G06F 17/50* (2006.01)
*G06T 19/20* (2011.01)
(Continued)

(52) U.S. Cl.
CPC .......... *G06T 19/20* (2013.01); *A61C 13/0004* (2013.01); *G06T 7/70* (2017.01)

(58) Field of Classification Search
CPC ...................................................... G06T 19/20
(Continued)

(56) References Cited

U.S. PATENT DOCUMENTS 5,823,778 A 10/1998 Schmitt et al.
6,842,175 B1 1/2005 Schmalstieg et al.
(Continued)

FOREIGN PATENT DOCUMENTS

DE 10 2004 038 136 A1 2/2006
EP 1 164 397 A1 12/2001
(Continued)

OTHER PUBLICATIONS

Cevidanes et al., "Three-dimensional surgical simulations", American Journal of Orthodontics and Dentofacial Orthopedics, vol. 138, Issue 3, Sep. 2007, pp. 361-371.*

(Continued)

*Primary Examiner* — Hugh M Jones
(74) *Attorney, Agent, or Firm* — Dentsply Sirona inc.

(57) ABSTRACT

The invention concerns a device (1) for editing a virtual 3-D model (2) of teeth (2.1, 2.2, 2.3, 2.4) positioned in a dental arch (9, 11) by means of a virtual tool (21, 22, 23, 24, 25, 26, 27, 28, 50). The tool (21, 22, 23, 24, 25, 26, 27, 28, 50) can be used on a first tooth (2.1, 2.3) of the 3-D model (2), whereby the corresponding application is carried out on a second mirrored tooth (2.2, 2.4), contralateral to the first tooth with respect to a plane of symmetry (12), that is, on the tooth on the other side of the plane of symmetry (12), which is positioned as a mirror image of the first tooth (2.1, 2.3) with respect to the plane of symmetry (12).

19 Claims, 2 Drawing Sheets

(51) Int. Cl.
  *G06T 7/70* (2017.01)
  *A61C 13/00* (2006.01)
(58) Field of Classification Search
  USPC ........................................................ 703/2, 1
  See application file for complete search history.

(56) References Cited

U.S. PATENT DOCUMENTS

| | | | |
|---|---|---|---|
| 7,086,863 | B2 | 8/2006 | Van der Zel |
| 7,801,632 | B2 | 9/2010 | Orth et al. |
| 9,668,836 | B2 * | 6/2017 | Willers .................. G06T 19/20 |
| 2002/0018061 | A1 | 2/2002 | Gantt |
| 2003/0207235 | A1 | 11/2003 | der Zel |
| 2004/0185422 | A1 | 9/2004 | Orth et al. |
| 2006/0008776 | A1 | 1/2006 | Orth et al. |
| 2009/0030661 | A1 | 1/2009 | Bouffiou et al. |

FOREIGN PATENT DOCUMENTS

| | | |
|---|---|---|
| EP | 1 252 867 A1 | 10/2002 |
| EP | 1 614 397 A1 | 1/2006 |
| WO | 2011-100976 A1 | 8/2011 |

OTHER PUBLICATIONS

Official German Examination Report issued by the German Patent Office dated Jun. 10, 2011.
Machine English Translation of the German Examination Report.
A. Storck, Effiziente 3D-Interaktions-und Visualisierundgstechniken fur benutzerzentrierte Modellierungssysteme, Dissertation TU Darmstadt, 2000, S. 138. aufgerufen uber, and English translation of p. 138.

* cited by examiner

DEVICE AND METHOD FOR EDITING A VIRTUAL, THREE-DIMENSIONAL DENTAL MODEL BY MEANS OF A VIRTUAL TOOL

FIELD OF THE INVENTION

The invention concerns a device for editing a virtual 3-D model of teeth positioned in a dental arch by means of a virtual tool, together with a corresponding process for editing a virtual 3-D model.

PRIOR ART

Methods for the construction of a 3-D model of a dental arch are known from the prior art, whereby the dental surfaces are incorporated or a surface is created artificially using the wax-up method prior to the preparation and is virtually transferred onto the surface of the 3-D model. Partly for this reason, the three-dimensional data of the dental surface are copied.

In the manual creation of a restoration by the dental technician, the dental technician tries to mold the dental surface of the restoration such that it corresponds with the dental surface of the contralateral tooth, while taking the morphology of the natural dentition into account. Structuring the restoration in precise symmetry with the contralateral tooth, however, is seldom achieved.

Particularly in a restoration in the anterior tooth region, the symmetry of the restoration is a crucial factor for an esthetic restoration. The symmetry has reference to a plane of symmetry, which corresponds to the central facial axis and which is positioned between quadrants 1 and 2 or between quadrants 3 and 4. In the virtual planning of the restoration using CAD tools, the changes made by the user must also be performed mirror-symmetrically on the contralateral tooth in order to ensure the symmetry. This requires a high level of skill in the application of the CAD tools and an esthetic perception on the part of the user.

A method for the construction of the surface of a tooth replacement consisting of three-dimensional data is known from DE 10 2004 938 136 A1, whereby the three-dimensional data of a dental surface of a stored tooth are used at least as part of the surface of the tooth replacement to be fabricated. For this purpose, the dimensions of the dental surface are first determined and are then positioned on a stored tooth replacement or in the region of a three-dimensional virtual preparation site. At the same time, the position of the digital dental surface in the tooth replacement or in the preparation site can be determined in at least one direction in space and/or one direction of rotation.

In one embodiment, a dental surface of the contralateral tooth is used as a mirror image in order to form the surface of the restoration. In the process, the selected dental surface is mirrored using mirror imaging means, whereby a selection dialog is displayed. The size of the selected dental surface can also be changed, such that the surface can be adapted to the adjacent teeth. Using alignment tools, the position of the selected dental surface can be changed horizontally, vertically, with respect to the tilt and with respect to the enlargement. The selected dental surface is transferred using the conventional CAD machining tools. After adapting the selected dental surface of the tooth contralateral to the tooth to be fabricated, the surface created is graphically amalgamated with the preparation, whereby the tooth replacement to be fabricated is formed.

One disadvantage of this process is that the selection, the transfer and the adaptation of the dental surface of the contralateral tooth, although virtual, are nevertheless expensive and time-consuming for the user.

Another disadvantage is that in the manual adaptation of the selected dental surface by mirroring, altering the alignment, the extension and the tilt, the tooth replacement can be deformed, such that the esthetic demand on the symmetry of the tooth to be fabricated with the contralateral tooth is not met.

Another disadvantage is that, for the creation of a restoration where there are multiple teeth to be replaced, all the steps mentioned for the entire method are to be performed for each individual tooth.

Hence, the object of this invention is to make available a device or a method for the symmetrical editing of a virtual 3-D model, which enables time-saving editing and guarantees a symmetry of the teeth to be fabricated with their contralateral teeth.

DESCRIPTION OF THE INVENTION

This object is achieved by means of the present invention.

In accordance with the invention, a device is provided for editing a virtual 3-D model of teeth positioned in a dental arch by means of a virtual tool. The tool can be used on a first tooth of the model, whereby the corresponding application is applied to a second tooth mirrored to the first contralateral tooth with respect to a plane of symmetry, that is to the tooth on the other side of the plane of symmetry, which is positioned in respect of the plane of symmetry as a mirror image of the first tooth.

The device according to the invention can be a computer system with operating controls, such as a keyboard and mouse, which is suitable for editing the virtual 3-D model of teeth. Thereby, the virtual 3-D model can be adapted by means of CAD software to a three-dimensional data set for a preparation site, which has been measured with an intraoral camera. The computer system may also feature a display unit.

The 3-D model of the dental arch can display at least two symmetrical teeth to be replaced, such as the incisors 12, 11, 21, 22 of the maxilla or 42, 41, 31, 32 of the mandible, in accordance with the FDI diagram. The 3-D model may also display a divergent number of teeth to be replaced on the left and right side, for example the teeth 13, 12, 11 on the right side of the maxilla and the adjacent teeth 21, 22 on the left side of the maxilla. Thereby, the application can be applied to the teeth 12, 11 mirrored by the teeth 21, 22 along the plane of symmetry.

The user can perform various editing steps by means of the virtual tool, such as rotation, enlarging, altering the position, reducing and altering the shape.

The application using the tool on a first tooth is mirrored across the plane of symmetry and is correspondingly carried out on the second tooth positioned symmetrically to the first tooth, such that this is also edited symmetrically to the first tooth.

The predefined virtual 3-D model is, as a rule, symmetrical, such that the plane of symmetry is positioned between the teeth 11 and 21 in the maxilla or between the teeth 41 and 31 in the mandible in accordance with the FDI diagram.

This symmetrical virtual 3-D model can be adjusted to the individual situation in the patient's oral cavity, by, for example, displacing the divergent part of the 3-D model using an offset and superimposing the actual course of the jaw in the patient's oral cavity from a visual three-dimensional image of the dental situation.

Alternately, in a first step, a draft of the application symmetrical along the set plane of symmetry can be created. In the second step, this draft can be shifted around an offset in order to adjust the symmetrical draft to the actual course of the jaw.

The plane of symmetry can also be manually set by the user.

The plane of symmetry can also be determined by means of a computer, by superimposing the mirror image of the right-hand section of the dental arch along the plane of symmetry onto the left-hand section of the dental arch.

One advantage of this device is that the second tooth is automatically adapted to the first contralaterally positioned tooth by the computer. Thus, the symmetry of the virtual 3-D model in respect of the plane of symmetry is guaranteed in the editing of one side with respect to the other side. The user must only edit one side using the virtual tool. The teeth contralaterally positioned on the other side of the plane of symmetry are automatically adapted by the computer, such that the length of time for the creation of the virtual 3-D model is shortened.

Advantageously, using a computer, the mirrored application of the tool on the contralateral tooth can be performed simultaneously with the application on the first tooth.

Thus, the parameters of the application of the tool on the first tooth do not have to be saved in order to perform the mirrored application of the tool on the contralateral tooth at a later point in time. The mirrored application on the contralateral tooth takes place simultaneously without delay, by converting the parameters of the application on the first tooth in compliance with the mirror image of a plane of symmetry and applying these to the contralateral tooth.

Advantageously, the tool can effect a rotation of the first tooth around a first axis of rotation and a corresponding mirrored rotation of the second contralateral tooth around a second mirrored axis of rotation.

Thus, the rotation of the first tooth relative to the plane of symmetry is mirrored and applied to the second contralateral tooth. The individual rotation parameters, such as the angle of the axis of rotation to the dental arch, the direction of rotation and the angle of rotation, are applied to the second contralateral tooth mirror-symmetrically with respect to the plane of symmetry.

Advantageously, the tool can effect an enlargement or a reduction of the first tooth and of the second contralateral tooth by a scale factor.

Thus, the size of the virtual tooth can be adjusted in order to adapt it to the dental arch. The change in size is simultaneously applied to the second contralateral tooth such that the adjustment to the size is made mirror-symmetrically.

Advantageously, the tool can effect a change in the position with the same alignment of the first tooth and a change in the position of the second contralateral tooth mirrored around the sectional planes.

Thus, the tooth can be shifted relative to the dental arch, whereby the alignment of the tooth remains the same, such that the tooth can be adjusted to the adjacent teeth and the second contralateral tooth can be correspondingly shifted in a mirrored direction.

Advantageously, the tool can effect a change in the shape of the surface of the first tooth and accordingly, effect a mirrored change in the shape of the surface of the second contralateral tooth.

Thus, the surface of the tooth can be virtually modified. For example, so-called freeform tools can be used in order to insert hollows, ridges and small grooves or fissures into the surface of the virtual tooth. These dentally esthetic changes in the surface are then correspondingly mirrored on the contralateral tooth, without the user's intervention, by computer.

Advantageously, the changes made by the application of the tool on the first tooth and on the second contralateral tooth can be displayed.

Thus, the changes are visible to the user on a display device, such as a monitor, and hence can be tracked.

The changes can also be undone. The mirrored changes to the contralateral tooth during editing using the tool are also displayed.

Advantageously, the plane of symmetry can be set by the user.

For example, the plane of symmetry can be virtually shifted and turned by the user in order to position the plane of symmetry between teeth 11 and 21 in the maxilla or between teeth 41 and 31 in the mandible, in accordance with the FDI diagram. Thereby, the plane of symmetry is positioned such that the mirror image of a left-hand section of the dental arch along the plane of symmetry is superimposed on the right-hand section of the dental arch.

Advantageously, the plane of symmetry can be determined by computer by reference to the course of the dental arch and/or by reference to the positioning and shape of adjacent teeth in the 3-D model of the teeth to be replaced and/or by reference to the positioning and shape of antagonists to the teeth of the 3-D model.

Thus, the plane of symmetry is automatically defined by means of the computer. In doing so, a computer algorithm can be used, which mirrors one section of the dental arch on any selected level and compares this section with the opposing section of the dental arch. The plane of symmetry is determined where there are consistencies in the mirror image with the opposing section.

One further object of the invention is a corresponding method for editing a virtual 3-D model of the teeth positioned in a dental arch by means of a virtual tool. The tool is applied to a first tooth of the model, whereby the corresponding application is carried out on a second tooth, mirrored to the first contralateral tooth with reference to a plane of symmetry, that is, on the tooth on the other side of the plane of symmetry, which is located in a mirrored position relative to the first tooth with reference to the plane of symmetry.

At the same time, symmetrical operators in the CAD area can be used. One advantage of the method according to the invention is that the time spent editing is reduced since the changes must only be made in one section of the dental arch, and these are automatically mirrored in the second section of the dental arch. A further advantage is that a perfect symmetry of both sections is produced and hence the dental esthetics are guaranteed.

Advantageously, the mirrored application of the tool on the contralateral tooth can be performed simultaneously by computer for application on the first tooth.

The simultaneous application on the contralateral tooth has the advantage that the changes do not have to be stored and are applied directly by computer, mirrored on the contralateral tooth.

Advantageously, the tool can effect a rotation of the first tooth and a corresponding mirrored rotation of the second contralateral tooth around an axis of rotation.

Using the tool, the rotation can be effected virtually by means of a rotation operator, whereby the rotation operator is applied to the contralateral tooth as a mirror image on the plane of symmetry.

Advantageously, the tool can effect an enlargement or a reduction of the first and of the second contralateral tooth by a scale factor.

The enlargement or the reduction can be effected by means of an enlargement operator on the first tooth, whereby this enlargement operator can simultaneously alter the size of the second contralateral tooth.

Advantageously, the tool can effect a change in the position with the same orientation of the first tooth and a mirrored change in the position of the second contralateral tooth around the plane of symmetry.

The process step of changing the position of the first tooth can be effected by means of a displacement operator, whereby this is applied as a mirror image of the second contralateral tooth.

Advantageously, the tool can effect a change in the shape of the surface of the first tooth and effect an analogous mirrored change in the shape of the surface of the second contralateral tooth.

For the esthetic matching of the surface of the first tooth, so-called freeform tools can be used in order to shape hollows, ridges and fissures. These changes are simultaneously carried out mirror-symmetrically on the second contralateral tooth.

Advantageously, the changes in the application of the tool on the first tooth and on the second contralateral tooth can be displayed.

Thanks to the display of the changes, the user can better track these changes. The changes can also be undone.

Advantageously, the plane of symmetry can be set by the user.

Using displacement operators and rotation operators, the user can change the virtual position of the plane of symmetry relative to the dental arch. A mirror image of one section of the dental arch can be displayed on the plane of symmetry as an aid for the user. Thus, the user can more easily determine where the plane of symmetry is positioned by trying to correlate the mirror image of a section of the dental arch with the opposing section of the dental arch.

Advantageously, the plane of symmetry can be determined by computer, by reference to the course of the dental arch and/or by reference to the positioning and shape of adjacent teeth of the 3-D model of the teeth to be replaced and/or by reference to the positioning and shape of antagonists of the teeth of the 3-D model.

Thus, the plane of symmetry is automatically determined by computer. The advantage is that, as a result, the time spent planning the virtual 3-D model is reduced using the method in accordance with the invention.

BRIEF DESCRIPTION OF THE DRAWINGS

The drawings depict examples of the realization of the invention. The drawings depict.

EXAMPLES

Figure 1:
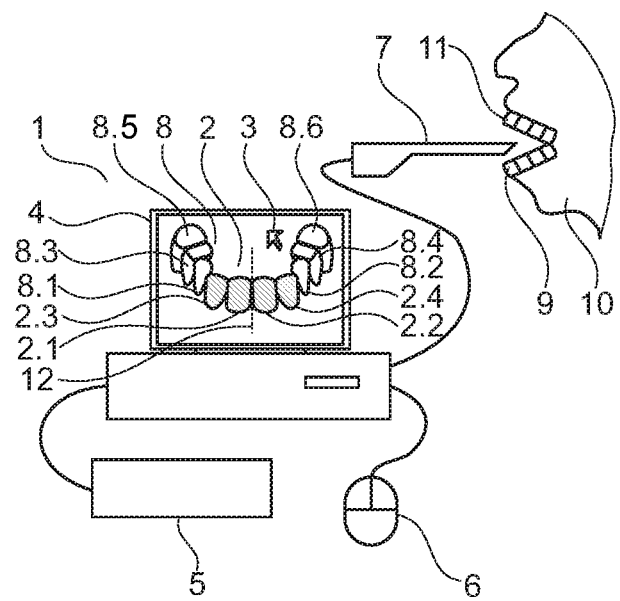
FIG. 1 Sketch of one embodiment of the device according to the invention, consisting of a computer, a monitor, a keyboard, a mouse and an intraoral camera.

FIG. 1 depicts an embodiment of the device 1 in accordance with the invention for symmetrical editing of a virtual 3-D model 2 of teeth 2.1, 2.2, 2.3 and 2.4 positioned in a dental arch by means of a virtual tool 3. The device 1 is realized as a computer, which is connected to a monitor 4, a keyboard 5, a mouse 6 and an intraoral camera 7 for recording visual three-dimensional images. The 3-D model 2 of the restoration, consisting of the teeth to be replaced 2.1, 2.2, 2.3 and 2.4, which are positioned between the teeth of a three-dimensional image 8 of a mandible 9 of a patient 10, whereby the visual image 8 comprises the teeth 8.1 to 8.6, which correspond to teeth 43, 44, 45 and 33, 34, 35 of the mandible in accordance with the FDI dental diagram. The teeth 2.1 to 2.4 to be replaced in the planned restoration correspond to the teeth 41, 31, 42, 32 in accordance with the FDI dental diagram. Correspondingly, the visual imaging and the planning for a restoration can also be carried out for the patient's 10 maxilla 11. A virtual plane of symmetry 12 is depicted between the teeth 2.1 and 2.2, which is positioned vertically to the viewing level of the monitor 4 and hence is depicted as a line. The teeth 2.2, 2.4 are positioned contralaterally to the teeth 2.1 and 2.3.

Figure 2:
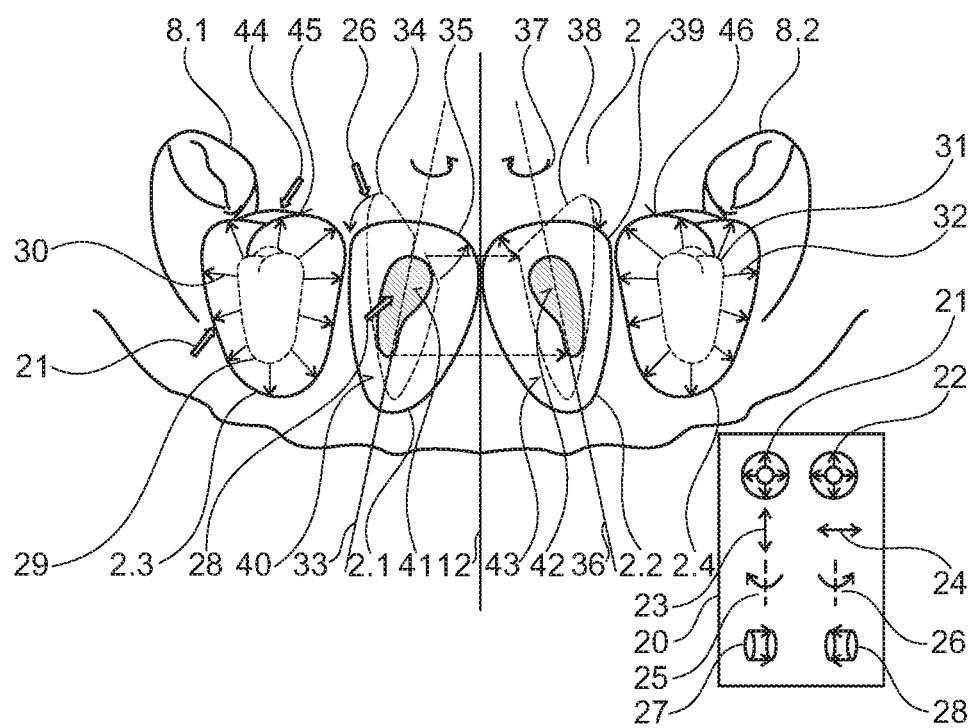
FIG. 2 Sketch of a virtual 3-D model of teeth positioned in a dental arch.

FIG. 2 depicts a sketch of the virtual 3-D model 2, consisting of the virtual teeth 2.1 to 2.4, which are positioned between the adjacent teeth 8.1 and 8.2 of the three-dimensional image 8 of the mandible 9. The plane of symmetry 12, which is vertical to the plane displayed and hence is depicted as a line, is positioned between the teeth 2.1 and 2.2. Several virtual tools are arranged in a drop-down menu 20, namely a first tool 21 for enlargement by a scale factor, a second tool 22 for reduction by a scale factor, a third tool 23 for changing the position in a vertical direction with the same alignment, a fourth tool 24 for changing the position in a horizontal direction, a fifth tool 25 for rotating a tooth around an axis in a clockwise direction, a sixth tool 26 for rotating a tooth around an axis in a counterclockwise direction, a seventh tool 27 for changing the shape of a surface, whereby a selected region is elevated, and an eighth tool 28 for editing the shape of a surface, whereby a selected region is lowered relative to the dental surface.

These tools are used for editing the virtual model 2. Multiple editing steps are depicted in FIG. 2. In the first editing step, the tool 21 was selected from the drop-down menu 20 and applied to the tooth 2.3 by the user using the operating controls 5 and 6 in FIG. 1, whereby an original model 29 of a tooth from a dental database, represented by a dashed line, was consistently enlarged by a particular scale factor. The enlargement is represented by the arrows 30. The tool 21 is represented by a first cursor. The user can, for example, select the original 3-D model 29 of the tooth from a dental database using the cursor and enlarge the 3-D model 29 to the desired size of the planned tooth 2.3 by moving the cursor away from the 3-D model. An enlargement operator of the software used is then used simultaneously on the contralateral tooth 2.4 and simultaneously effects a corresponding enlargement of a model 31 of a contralateral tooth, which depicts a mirror image of the original tooth 29 relative to the plane of symmetry 12. The enlargement of the mirrored tooth 31 is depicted by the arrows 32. Hence, the application of the tool 21 effects an enlargement of the tooth 2.3 and a simultaneous enlargement of the contralateral mirrored tooth 2.4 by the same scale factor.

In a second step of the process, the tool 26 for rotation around a selected axis is used on the tooth 2.1, whereby the tool 26 is depicted by a second cursor. Thereby, the user can set an axis of rotation 33 in order to turn the tooth 2.1 from an initial position 34, represented by a dashed line, by rotation in a counterclockwise direction around the selected axis 33 into the end position 35, represented by a solid line. The application of the tool 26 on the tooth 2.1 also effects a mirrored rotation of the contralateral tooth 2.2 around an axis of rotation 36, mirrored across from the plane of symmetry 12, in a clockwise direction, as represented by the arrow 37, whereby the tooth 2.2 is moved from an initial position 38, represented by a dashed line, into an end position 39. Hence, the application of the tool 26 effects both the rotation of the tooth 2.1 and the mirrored rotation of the contralateral tooth 2.2.

In a third step, the tool 28 is applied to a labial surface 40 of the tooth 2.1, whereby a selected region 41, represented by the dashed line, is lowered relative to the labial surface 40. The tool 28 is represented by a third cursor. In applying the tool 28 to the tooth 2.1, a region 42 of the contralateral tooth 2.2 mirrored relative to the plane of symmetry 12 is simultaneously lowered on the contralateral tooth 2.2 relative to the labial surface 43 of the tooth 2.2 by the same height as the selected region 41. The tool 28 is a so-called freeform tool and this effects the change in the surface 40 of the tooth 2.1 and, simultaneously, a mirrored change in the surface 43 of the contralateral tooth 2.2.

In a further step, hollows (fissures) are incorporated into the occlusal surface 45 of the tooth 2.3 by means of another freeform tool 44. Simultaneously with the change to the occlusal surface 45, an occlusal surface 46 of the contralateral tooth 2.4 is correspondingly mirror-symmetrically changed by incorporating the mirrored hollows into the occlusal surface 46. Hence, the application of the tool 44 effects a change in the occlusal surface 45 of the tooth 2.3 and a simultaneous mirrored change in the occlusal surface 46 of the contralateral tooth 2.4.

Figure 3:
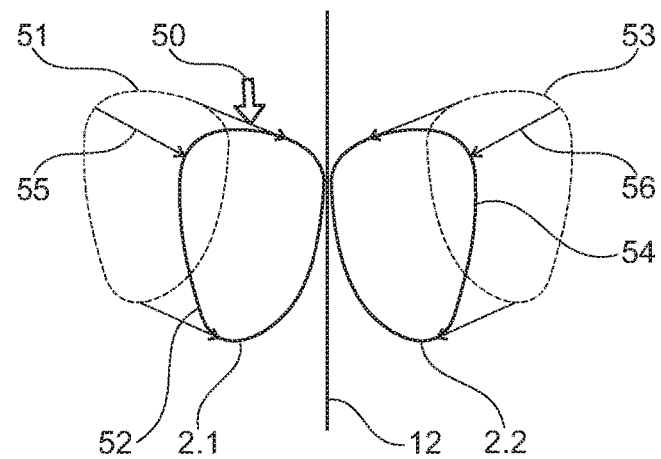
FIG. 3 Sketch of the application of a virtual shifting tool.

In FIG. 3, the application of the tools 24 for changing the position of the tooth with the same orientation is represented, whereby the tool is indicated by a cursor 50. By means of the cursor 50, the user can shift the tooth 2.1 from an initial position 51, represented by a dashed line, to an end position 52, represented by a solid line, whereby the orientation of the tooth remains unchanged. In applying the tool 2.1 for changing the position by means of the cursor 50 to the tooth, the contralateral tooth 2.2 mirrored relative to the plane of symmetry 12 is simultaneously shifted from an initial position 53 to an end position 54. The displacement of the tooth 2.1 is represented by the arrows 55 and that of the tooth 2.2 by the arrows 56.

Figure 4:
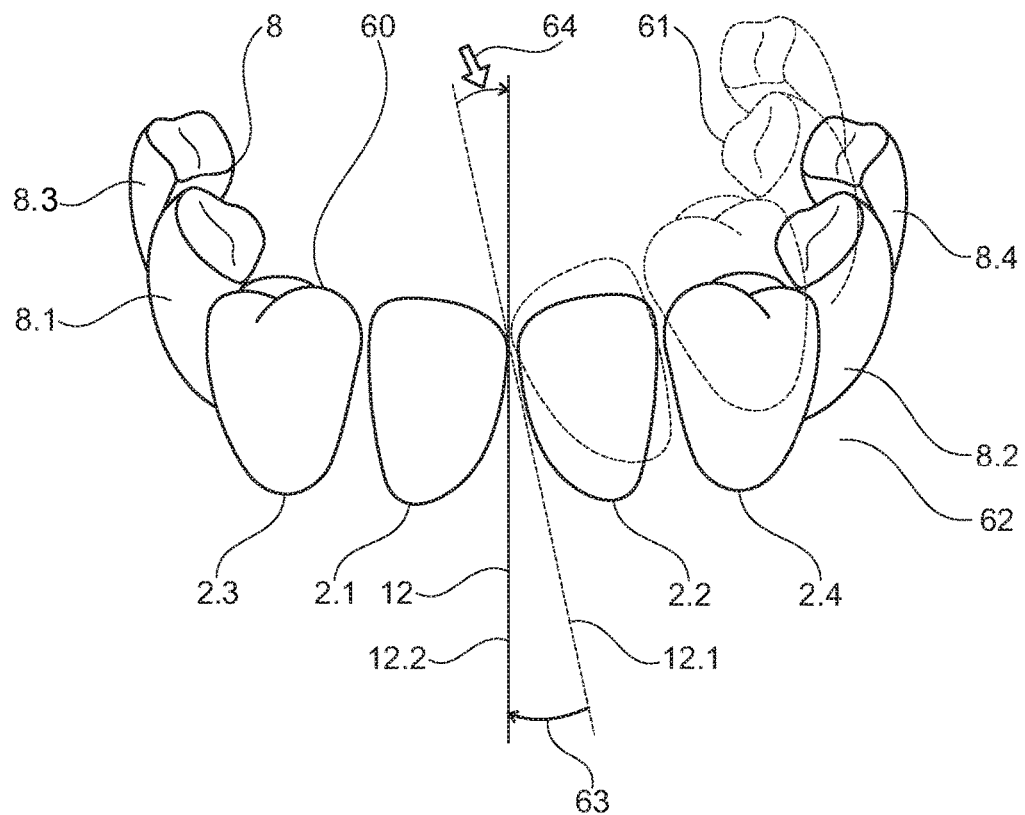
FIG. 4 Sketch of the depiction of the identification of the plane of symmetry.

In FIG. 4, a step of the process is represented, in which the plane of symmetry 12 is determined by the user. In order to facilitate locating the plane of symmetry, the left side of the dental arch 60, consisting of the teeth 2.1 and 2.3 to be replaced and the teeth 8.1 and 8.2 in the visual three-dimensional image 8 in FIG. 1, is mirrored on the axis of symmetry 12.1 in an initial position. The mirror image 61 of the left section 60 of the dental arch is represented by a dashed line. Based on the initial position 12.1, the plane of symmetry 12 is turned and shifted until it reaches an end position 12.2, in which the mirror image 61 of the left section 60 of the dental arch coincides as much as possible with the right section 62. The right section 62 is represented as a solid line and consists of the teeth 2.2 and 2.4 of the 3-D model 2 to be replaced, together with the teeth 8.2 and 8.4 in the three-dimensional visual image 8 in FIG. 1. The rotation of the plane of symmetry 12 is represented by the arrow 63 and is operated by means of a virtual tool 64, to change the position of the plane of symmetry. The plane of symmetry 12 can also be determined by computer, whereby the position of the plane of symmetry 12 is changed by means of a computer algorithm until the mirror image 61 of the left section 60 of the dental arch coincides as much as possible with the right section 62 of the dental arch. Image data for the positioning and the shape of the dental arch and of adjacent teeth and antagonists can also be taken into account in the computer-aided determination of the plane of symmetry.

LIST OF REFERENCE SYMBOLS

1 Device
2 3-D model
2.1-2.4 Teeth of the 3-D model
3 Tool
4 Screen
5 Keyboard
6 Mouse
7 Intraoral camera
8 Image
8.1-8.6 Teeth in the image
9 Mandible
10 Patient
11 Maxilla
12 Plane of symmetry
12.1 Initial position of the axis of symmetry
12.2 End position of the axis of symmetry
20 Drop-down menu
21 First tool
22 Second tool
23 Third tool
24 Fourth tool
25 Fifth tool
26 Sixth tool
27 Seventh tool
28 Eighth tool
29 Original model of a tooth
30 Arrow
31 Mirror image of the model 29
32 Arrow
33 Axis of rotation
34 Initial position of the tooth
35 End position of the tooth
36 Mirrored axis of rotation
37 Direction arrow
38 Initial position
39 End position
40 Labial surface
41 Selected region
42 Mirrored region
43 Labial surface
44 Freeform tool
45 Occlusal surface
46 Occlusal surface
50 Cursor
51 Initial position
52 End position
53 Initial position
54 End position
55 Arrow
56 Arrow
60 Left section
61 Mirror image/Dental arch
62 Right section
63 Arrow
64 Tool

The invention claimed is:

1. An apparatus, comprising:
a computer configured to:
generate three-dimensional images of a patient's teeth using an intraoral camera;
obtain a three-dimensional model of teeth based on the generated three-dimensional images of the patient's teeth;
perform an edit of a first tooth in the three-dimensional model of teeth positioned in a dental arch; and
automatically perform a corresponding edit of a second tooth, in response to the edit of the first tooth,
wherein the corresponding edit is automatically performed in mirrored fashion with respect to a plane of symmetry, by applying adjusting parameters to the second tooth,
wherein said adjusting parameters correspond to parameters of the edit of the first tooth by mirror symmetry,
wherein the second tooth is contralateral to the first tooth with respect to a plane of symmetry, and is positioned as a mirror image of the first tooth with respect to the plane of symmetry.

2. The apparatus in accordance with claim 1, wherein the edit of the first tooth effects a rotation of the first tooth around a first axis of rotation and the edit of the second tooth effects a corresponding mirrored rotation of the second tooth around a second axis of rotation.

3. The apparatus in accordance with claim 1, wherein the edit of the first tooth effects an enlargement or a reduction of the first tooth by a scale factor and the edit of the second tooth effects an enlargement or a reduction of the second tooth by the scale factor.

4. The apparatus in accordance with claim 1, wherein the edit of the first tooth effects a change in a position of the first tooth with a same orientation and the edit of the second tooth effects a mirrored change in a position of the second tooth around the plane of symmetry.

5. The apparatus in accordance with claim 1, wherein the edit of the first tooth effects a change in a shape of a surface of the first tooth and the edit of the second tooth effects a corresponding mirrored change in a shape of a surface of the second tooth.

6. The apparatus in accordance with claim 1, further comprising:
a display device,
wherein the computer is further configured to display an edited first tooth and an edited second tooth on the display device.

7. The apparatus in accordance with claim 1, wherein the computer is further configured to receive an instruction representing the plane of symmetry.

8. The apparatus in accordance with claim 1, wherein the computer is further configured to determine the plane of symmetry by reference to one or more of:
(i) a course of the dental arch,
(ii) a position and a shape of a tooth adjacent to the first tooth in the three-dimensional model, and
(iii) positions and shapes of antagonists to the teeth in the three-dimensional model.

9. The apparatus in accordance with claim 1, wherein the plane of symmetry is defined by locations where there are consistencies in a mirrored first section of the dental arch with an opposing section of the dental arch.

10. A method of editing a dental model, comprising:
generating three-dimensional images of a patient's teeth using an intraoral camera;
obtaining a three-dimensional model of teeth based on the three-dimensional images of the patient's teeth;
editing a first tooth in the three-dimensional model of teeth positioned in a dental arch; and
automatically performing a corresponding edit of a second tooth, in response to the edit of the first tooth,
wherein the corresponding edit is automatically performed in mirrored fashion with respect to a plane of symmetry, by applying adjusting parameters to the second tooth,
wherein said adjusting parameters correspond to parameters of the edit of the first tooth by mirror symmetry,
wherein the second tooth is contralateral to the first tooth with respect to a plane of symmetry and is positioned as a mirror image of the first tooth with respect to the plane of symmetry, and
wherein the plane of symmetry is defined by locations where there are consistencies in a mirrored first section of the dental arch with an opposing section of the dental arch.

11. The method in accordance with claim 10, wherein the editing of the first tooth effects a rotation of the first tooth around a first axis of rotation and the editing of the second tooth effects a corresponding mirrored rotation of the second tooth around a second axis of rotation.

12. The method in accordance with claim 10, wherein the editing of the first tooth effects an enlargement or a reduction of the first tooth by a scale factor and the editing of the second tooth effects an enlargement or a reduction of the second tooth by the scale factor.

13. The method in accordance with claim 10, wherein the editing of the first tooth effects a change in a position of the first tooth with a same orientation and the editing of the second tooth effects a mirrored change in a position of the second tooth around the plane of symmetry.

14. The method in accordance with claim 10, wherein the editing of the first tooth effects a change in a shape of a surface of the first tooth and the editing of the second tooth effects a corresponding mirrored change in a shape of a surface of the second tooth.

15. The method in accordance with claim 10, further comprising: displaying an edited first tooth and an edited second tooth on a display device.

16. The method in accordance with claim 10, further comprising: receiving an instruction representing the plane of symmetry.

17. The method in accordance with claim 10, further comprising:
determining the plane of symmetry based on one or more of:
(i) a course of the dental arch,
(ii) a position and a shape of a tooth adjacent to the first tooth in the three-dimensional model, and
(iii) positions and shapes of antagonists to the teeth in the three-dimensional model.

18. The method in accordance with claim 10, wherein the plane of symmetry is defined by locations where there are consistencies in a mirrored first section of the dental arch with an opposing section of the dental arch.

19. A method of editing a dental model, comprising:
generating three-dimensional images of a patient's teeth using an intraoral camera;
obtaining a three-dimensional model of teeth based on the three-dimensional images of the patient's teeth;
determining a plane of symmetry by:

mirroring a left section of a dental arch on an axis of symmetry to produce a mirror image of the left section that corresponds to the axis of symmetry, and turning the axis of symmetry from an initial position to an end position such that the mirror image of the left section coincides or substantially coincides with a right section of the dental arch;

editing a first tooth in the three-dimensional model of teeth positioned in the dental arch; and automatically and simultaneously editing, in response to the editing of the first tooth in the three-dimensional model, a second tooth in the three-dimensional model in a corresponding manner to the edit of the first tooth, wherein the second tooth is contralateral to the first tooth with respect to the plane of symmetry and is positioned as a mirror image of the first tooth with respect to the plane of symmetry.

\* \* \* \* \*